United States Patent
Nielsen et al.

(10) Patent No.: US 8,535,911 B2
(45) Date of Patent: Sep. 17, 2013

(54) CELL WITH IMPROVED SECRETION MEDIATED BY MRGA PROTEIN OR HOMOLOGUE

(75) Inventors: Allan Kent Nielsen, Soborg (DK); Michael Dolberg Rasmussen, Vallensbaek (DK)

(73) Assignee: Novosymes A/S, Bagsvaerd (DK)

( * ) Notice: Subject to any disclaimer, the term of this patent is extended or adjusted under 35 U.S.C. 154(b) by 0 days.

(21) Appl. No.: 13/571,777

(22) Filed: Aug. 10, 2012

(65) Prior Publication Data

US 2013/0217097 A1    Aug. 22, 2013

Related U.S. Application Data

(62) Division of application No. 10/582,277, filed as application No. PCT/DK2004/000859 on Dec. 10, 2004, now Pat. No. 8,268,583.

(60) Provisional application No. 60/529,141, filed on Dec. 12, 2003.

(30) Foreign Application Priority Data

Dec. 10, 2003  (DK) ................................ 2003 01824

(51) Int. Cl.
*C12P 21/02*  (2006.01)
(52) U.S. Cl.
USPC ....................................... 435/69.1; 435/71.1

(58) Field of Classification Search
None
See application file for complete search history.

(56) References Cited

FOREIGN PATENT DOCUMENTS

WO    94/19471 A1    9/1994
WO    99/04007 A1    1/1999

OTHER PUBLICATIONS

Chen et al, 1993, Database Medline—Access No. L19547.
Chen et al, 1995, Mol Biol 18(2), 295-300.
Chen et al, 1995, Proc Natl Acad Sci 92, 8190-8194.
Essen et al, 2007, Protein Data Bank—deposit 2chp.
Hartford et al, 1994, Microbiology 140, 297-304.
Naclerio et al, 1995, Appl Environ Microbiol 61(12), 4471-4473.
Perkins et al, 1986, Proc Natl Acad Sci 83, 140-144.
Pugsley et al, 2003, Mol Microbiol 52(1), 3-11.
Sakaguchi et al, 1997, Curr Op Biotechnol 8, 595-601.
Van Wely et al, 2000, Microbiology 146, 2573-2581.

*Primary Examiner* — Suzanne M Noakes
(74) *Attorney, Agent, or Firm* — Eric J. Fechter; Michael W. Krenicky

(57) ABSTRACT

A progeny cell derived from a parent cell, wherein the progeny cell comprises at least one gene encoding MrgA protein or a functional homologue thereof and/or a DNA segment operably linked with the encoding gene, wherein said gene and/or DNA segment is manipulated with respect to the parent cell; the progeny cell comprises two or more copies of a gene encoding MrgA protein or a functional homologue thereof; or the progeny cell is mutated with respect to the parent cell; whereby the progeny cell produces greater amounts of MrgA protein or a functional homologue thereof than the parent cell.

11 Claims, No Drawings

CELL WITH IMPROVED SECRETION MEDIATED BY MRGA PROTEIN OR HOMOLOGUE

CROSS-REFERENCE TO RELATED APPLICATIONS

This application is a division of U.S. application Ser. No. 10/582,277 filed Jun. 10, 2006 (now allowed) which is a 35 U.S.C. 371 national application of PCT/DK2004/000859 filed Dec. 10, 2004 which claims priority or the benefit under 35 U.S.C. 119 of Danish application no. PA 2003 01824 filed Dec. 10, 2003 and U.S. provisional application No. 60/529,141 filed Dec. 12, 2003, the contents of which are fully incorporated herein by reference.

FIELD OF THE INVENTION

In the industrial production of secreted polypeptides it is of interest to achieve a product yield as high as possible. Accordingly, it is highly desirable to remove any potential bottlenecks from the secretory machinery of production cells. To this end it is well-known that it can be advantageous to overexpress one or more gene(s) encoding protein(s) involved with secretion, e.g., PrsA protein or functional homologues thereof. The present invention relates to a cell which overexpresses MrgA protein or functional MrgA protein homologue.

BACKGROUND OF THE INVENTION

The MrgA protein of *Bacillus subtilis* was originally classified as a Dps(PexB) homologue, encoded by a metalloregulated oxidative-stress gene (metallo regulated gene) mrgA. One purported function of the MrgA protein in *B. subtilis* is to bind DNA under conditions of oxidative stress and to protect the DNA against damage (Chen L, Helmann J D. 1995. *Bacillus subtilis* MrgA is a Dps(PexB) homologue: evidence for metalloregulation of an oxidative stress gene. Mol Microbiol 18: 295-300).

A *B. subtilis* mrgA deletion mutant only had a somewhat reduced overall level of secreted proteins, and it was therefore broadly concluded that MrgA is not involved in protein secretion in *B. subtilis*, (van Wely K H, Swaying J, Klein M, Freud I R, Driessen A J. 2000. The carboxyl terminus of the *Bacillus subtilis* SecA is dispensable for protein secretion and viability. Microbiology 146: 2573-81).

However, the present inventors have found, as demonstrated herein, that MrgA is in fact involved in secretion in *Bacillus*, and that a higher expression of mrgA leads to a higher secretion of an exoenzyme, exemplified below by improved secretion of a heterologous alpha-amylase.

SUMMARY OF THE INVENTION

Severe secretion stress was imposed on a *Bacillus subtilis* cell by overexpressing an exoenzyme, the alpha-amylase AmyQ of *Bacillus amyloliquefaciens*, encoded by a plasmid-borne constitutively expressed gene in the cell. DNA microarray analyses revealed an increased expression of the general stress protein mrgA as a response to the imposed secretion stress.

The mrgA gene was amplified by PCR from the chromosome of *B. subtilis*. Three PCR reactions were carried out with three different upstream PCR primers, each comprising the sequence of a synthetic constitutive promoter of different strength. The three amplified PCR fragments were integrated into the chromosome of individual *B. subtilis* strains, resulting in three recombinant strains, each expressing mrgA from the native locus, and from the integrated mrgA copy, which was transcribed from the synthetic promoter.

The three strains overexpressing mrgA, and a corresponding control strain, were then transformed with the plasmid pKTH10, which carries and constitutively overexpresses the gene encoding the alpha-amylase AmyQ of *B. amyloliquefaciens*.

The yields of secreted AmyQ amylase from the transformed strains were determined after 1 weeks cultivation in 200 ml BPX culture flasks. For each of the three MrgA overexpressing strains, and the control strain, three independent isolates were analysed in triplicate to determine the amylase yields. The yields of secreted amylase from the MrgA overexpressing strains were 27%-44% higher than the yield from the control strain.

Accordingly, in a first aspect the invention relates to a progeny cell derived from a parent cell, wherein
   a) the progeny cell comprises at least one gene encoding MrgA protein or a functional homologue thereof and/or a DNA segment operably linked with the encoding gene, wherein said gene and/or DNA segment is manipulated with respect to the parent cell;
   b) the progeny cell comprises two or more copies of a gene encoding MrgA protein or a functional homologue thereof; or
   c) the progeny cell is mutated with respect to the parent cell;
   whereby the progeny cell produces greater amounts of MrgA protein or a functional homologue thereof than the parent cell.

In the present context, a functional homologue of the MrgA protein is a protein, which when expressed at a higher level in a cell, leads to an increased secretion of an exoenzyme, such as an alpha-amylase, when compared with an otherwise identical cell with normal expression of the MrgA functional homologue cultivated under essentially identical conditions. In addition, the functional homologue of the MrgA protein shares an amino acid sequence identity with the MrgA protein of at least 50%, preferably 55%, 60%, 65%, 70%, 75%, 80%, 85%, 90%, 95%, 97%, or most preferably 99% when aligned as described above.

A second aspect of the invention relates to a method for enhancing secretion of an protein of interest, the method comprising expressing said protein in a cell according to the first aspect.

A third aspect of the invention relates to a method for producing a cell as defined in the first aspect useful for production of an protein of interest, said method comprising a step of manipulating a cell to increase the expression of MrgA protein or functional homologue thereof.

In a fourth aspect the invention relates to a method for producing an protein of interest, comprising the steps of:
a) cultivating a cell as defined in the first aspect; and
b) recovering the protein.

In a final aspect the invention relates to the use of MrgA-protein or a functional homologue thereof in a method for enhancing secretion of an protein by manipulating or mutating a cell to express greater amounts of MrgA protein or functional homologue thereof than the non-manipulated or non-mutated cell.

DEFINITIONS

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989") DNA Cloning: A Practical Approach, Volumes I and II/D. N. Glover ed. 1985); Oligonucleotide Synthesis (M. J. Gait ed. 1984); Nucleic Acid Hybridization (B. D. Hames & S. J. Higgins eds (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984).

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

A "nucleic acid molecule" or "nucleotide sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization.

For purposes of the present invention, hybridization indicates that the nucleotide sequence hybridizes to a labeled polynucleotide probe which hybridizes to the nucleotide sequence shown in SEQ ID NO:1 under very low to very high stringency conditions. Molecules to which the polynucleotide probe hybridizes under these conditions may be detected using X-ray film or by any other method known in the art. Whenever the term "polynucleotide probe" is used in the present context, it is to be understood that such a probe contains at least 15 nucleotides.

In an interesting embodiment, the polynucleotide probe is the complementary strand of a fragment of at least 15 nucleotides of SEQ ID NO:1. In another interesting embodiment, the polynucleotide probe is a fragment of at least 15 nucleotides of the complementary strand of any nucleotide sequence which encodes the polypeptide of SEQ ID NO:2. In a further interesting embodiment, the polynucleotide probe is the complementary strand of SEQ ID NO:1. In a still further interesting embodiment, the polynucleotide probe is the complementary strand of the mature polypeptide coding region of SEQ ID NO:1.

For long probes of at least 100 nucleotides in length, very low to very high stringency conditions are defined as prehybridization and hybridization at 42° C. in 5×SSPE, 1.0% SDS, 5×Denhardt's solution, 100 □g/ml sheared aid denatured salmon sperm DNA, following standard Southern blotting procedures. Preferably, the long probes of at least 100 nucleotides do not contain more than 1000 nucleotides. For long probes of at least 100 nucleotides in length, the carrier material is finally washed three times each for 15 minutes using 2×SSC, 0.1% SDS at 42° C. (very low stringency), preferably washed three times each for 15 minutes using 0.5×SSC, 0.1% SDS at 42° C. (low stringency), more preferably washed three times each for 15 minutes using 0.2×SSC, 0.1% SDS at 42° C. (medium stringency), even more preferably washed three times each for 15 minutes using 0.2×SSC, 0.1% SDS at 55° C. (medium-high stringency), most preferably washed three times each for 15 minutes using 0.1×SSC, 0.1% SDS at 60° C. (high stringency), in particular washed three times each for 15 minutes using 0.1×SSC, 0.1% SDS at 68° C. (very high stringency).

Although not particularly preferred, it is contemplated that shorter probes, e.g. probes which are from about 15 to 99 nucleotides in length, such as from about 15 to about 70 nucleotides in length, may be also be used. For such short probes, stringency conditions are defined as prehybridization, hybridization, and washing post-hybridization at 5° C. to 10° C. below the calculated Tm using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to 99 nucleotides in length, the carrier material is washed once in 6×SCC plus 0.1% SDS for 15 minutes and twice each for 15 minutes using 6×SSC at 5° C. to 10° C. below the calculated Tm.

A DNA "coding sequence" or an "open reading frame (ORF)" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

An expression vector is a DNA molecule, linear or circular, that comprises a segment encoding a polypeptide of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA, or may contain elements of both.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "secretory signal sequence" is a DNA sequence that encodes a polypeptide (a "secretory peptide" that, as a component of a larger polypeptide, directs the larger polypeptide through a secretory pathway of a cell in which it is synthesized. The larger polypeptide is commonly cleaved to remove the secretory peptide during transit through the secretory pathway.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A chromosomal gene is rendered non-functional if the polypeptide that the gene encodes can no longer be expressed in a functional form. Such non-functionality of a gene can be induced by a wide variety of genetic manipulations as known in the art, some of which are described in Sambrook et al. vide supra. Partial deletions within the ORF of a gene will often render the gene non-functional, as will mutations.

The term "an expressible copy of a chromosomal gene" is used herein as meaning a copy of the ORF of a chromosomal gene, wherein the ORF can be expressed to produce a fully functional gene product. The expressible copy may not be transcribed from the native promoter of the chromosomal gene, it may instead be transcribed from a foreign or heterologous promoter, or it may indeed be promoterless and expressed only by transcriptional read-through from a gene present upstream of the 5' end of the ORF. Transcriptional read-through is intended to have the same meaning here as the generally recognized meaning in the art.

"Operably linked", when referring to DNA segments, indicates that the segments are arranged so that they function in concert for their intended purposes, e.g. transcription initiates in the promoter and proceeds through the coding segment to the terminator.

A coding sequence is "under the control" of transcriptional and translational control sequences in a cell when RNA polymerase transcribes the coding sequence into mRNA, which is then trans-RNA spliced and translated into the protein encoded by the coding sequence.

"Heterologous" DNA refers to DNA not naturally located in the cell, or in a chromosomal site of the cell. Preferably, the heterologous DNA includes a gene foreign to the cell.

As used herein the term "nucleic acid construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a polypeptide of interest. The construct may optionally contain other nucleic acid segments.

The nucleic acid construct of the invention encoding the polypeptide of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., supra).

The nucleic acid construct of the invention encoding the polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques. The nucleic acid construct may also be prepared by polymerase chain reaction using specific primers, for instance as described in U.S. Pat. No. 4,683,202 or Saiki et al., Science 239 (1988), 487-491.

The term nucleic acid construct may be synonymous with the term "expression cassette" when the nucleic acid construct contains the control sequences necessary for expression of a coding sequence of the present invention The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcription and translation control sequences which mediate the expression of the polypeptide. The promoter may be any nucleic acid sequence which shows transcriptional activity in the host cell of choice and may be obtained from genes encoding extracellular or intracellular polypeptides either homologous or heterologous to the host cell.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the expressed polypeptide into the cell's secretory pathway of the host cell. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. A foreign signal peptide coding region may be required where the coding sequence does not normally contain a signal peptide coding region. Alternatively, the foreign signal peptide coding region may simply replace the natural signal peptide coding region in order to obtain enhanced secretion of the exoprotein relative to the natural signal peptide coding region normally associated with the coding sequence. The signal peptide coding region may be obtained from a glucoamylase or an amylase gene from an *Aspergillus* species, a lipase or proteinase gene from a *Rhizomucor* species, the gene for the alpha-factor from *Saccharomyces cerevisiae*, an amylase or a protease gene from a *Bacillus* species, or the calf preprochymosin gene. However, any signal peptide coding region capable of directing the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophilum* laccase gene (WO 95/33836).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be placed in tandem with the regulatory sequence.

Examples of suitable promoters for directing the transcription of the gene(s) of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus subtilis* alkaline protease gene, the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus amyloliquefaciens* BAN amylase gene, the *Bacillus licheniformis* penicillinase gene (penP), the *Bacillus subtilis* xylA and xylB genes, and the prokaryotic beta-lactamase gene (VIIIa-Kamaroff et al., 1978, Proceedings of the National Academy of Sciences USA 75:3727-3731), as well as the tac promoter (DeBoer et al., 1983, Proceedings of the National Academy of Sciences USA 80:21-25). Further promoters are described in "Useful proteins from recombinant bacteria" in Scientific American, 1980, 242:74-94; and in Sambrook et al., 1989, supra.

An effective signal peptide coding region for bacterial host cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* PrsA gene. Further signal peptides are described by Simonen and Palva, 1993, Microbiological Reviews 57:109-137.

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Antibiotic selectable markers confer antibiotic resistance to such antibiotics as ampicillin, kanamycin, chloramphenicol, tetracycline, neomycin, hygromycin or methotrexate. Suitable markers for yeast host cells are ADE2, HIS3, LEU2, LYS2, MET3, TRP1, and URA3.

The vectors of the present invention preferably contain an element(s) that permits stable integration of the vector, or of a smaller part of the vector, into the host cell genome or autonomous replication of the vector in the cell independent of the genome of the cell.

The vectors, or smaller parts of the vectors such as amplification units of the present invention, may be integrated into the host cell genome when introduced into a host cell. For chromosomal integration, the vector may rely on the nucleic acid sequence encoding the polypeptide or any other element of the vector for stable integration of the vector into the genome by homologous or nonhomologous recombination.

Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences; specific examples of encoding sequences suitable for site-specific integration by homologous recombination are given in WO 02/00907 (Novozymes, Denmark), which is hereby incorporated by reference in its totality.

On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences. The copy number of a vector, an expression cassette, an amplification unit, a gene or indeed any defined nucleotide sequence is the number of identical copies that are present in a host cell at any time. A gene or another defined chromosomal nucleotide sequence may be present in one, two, or more copies on the chromosome. An autonomously replicating vector may be present in one, or several hundred copies per host cell.

An amplification unit of the invention is a nucleotide sequence that can integrate into the chromosome of a host cell, whereupon it can increase in number of chromosomally integrated copies by duplication of multiplication. The unit comprises an expression cassette as defined herein comprising at least one copy of a gene of interest and an expressable copy of a chromosomal gene, as defined herein, of the host cell. When the amplification unit is integrated into the chromosome of a host cell, it is defined as that particular region of the chromosome which is prone to being duplicated by homologous recombination between two directly repeated regions of DNA. The precise border of the amplification unit with respect to the flanking DNA is thus defined functionally, since the duplication process may indeed duplicate parts of the DNA which was introduced into the chromosome as well as parts of the endogenous chromosome itself, depending on the exact site of recombination within the repeated regions. This principle is illustrated in Janniére et al. (1985, Stable gene amplification in the chromosome of Bacillus subtilis. Gene, 40: 47-55), which is incorporated herein by reference.

For autonomous replication, the vector may further comprise an origin of replication enabling the vector to replicate autonomously in the host cell in question. Examples of bacterial origins of replication are the origins of replication of plasmids pBR322, pUC19, pACYC177, pACYC184, pUB110, pE194, pTA1060, and pAMbeta1. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, Proceedings of the National Academy of Sciences USA 75:1433).

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The transformation of a bacterial host cell may, for instance, be effected by protoplast transformation (see, e.g., Chang and Cohen, 1979, Molecular General Genetics 168: 111-115), by using competent cells (see, e.g., Young and Spizizin, 1961, Journal of Bacteriology 81:823-829, or Dubnar and Davidoff-Abelson, 1971, Journal of Molecular Biology 56:209-221), by electroporation (see, e.g., Shigekawa and Dower, 1988, Biotechniques 6:742-751), or by conjugation (see, e.g., Koehler and Thorne, 1987, Journal of Bacteriology 169:5771-5278).

The transformed or transfected host cells described above are cultured in a suitable nutrient medium under conditions permitting the expression of the desired polypeptide, after which the resulting polypeptide is recovered from the cells, or the culture broth.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media are prepared using procedures known in the art (see, e.g., references for bacteria and yeast; Bennett, J. W. and LaSure, L., editors, More Gene Manipulations in Fungi, Academic Press, CA, 1991).

If the polypeptide is secreted into the nutrient medium, the polypeptide can be recovered directly from the medium. If the polypeptide is not secreted, it is recovered from cell lysates. The polypeptide are recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989).

In the present context, the term "substantially pure polypeptide" means a polypeptide preparation which contains at the most 10% by weight of other polypeptide material with which it is natively associated (lower percentages of other polypeptide material are preferred, e.g. at the most 8% by weight, at the most 6% by weight, at the most 5% by weight, at the most 4% at the most 3% by weight, at the most 2% by weight, at the most 1% by weight, and at the most ½% by weight). Thus, it is preferred that the substantially pure polypeptide is at least 92% pure, i.e. that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form", i.e. that the polypeptide preparation is essentially free of other polypeptide material with which it is natively associated. This can be accomplished, for example, by preparing the polypeptide by means of well-known recombinant methods. Herein, the term "substantially pure polypeptide" is synonymous with the terms "isolated polypeptide" and "polypeptide in isolated form".

In the present context, the homology between two amino acid sequences or between two nucleotide sequences is described by the parameter "identity". For purposes of the present invention, alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is –12 for proteins and –16 for DNA, while the penalty for additional residues in a gap is –2 for proteins and –4 for DNA. Alignment may be made with the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

Multiple alignments of protein sequences may be made using "ClustalW" (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680). Multiple alignment of DNA sequences may be done using the protein alignment as a template, replacing the amino acids with the corresponding codon from the DNA sequence.

In the present context, a functional homologue of the MrgA protein is a protein, which when expressed at a higher level in a cell, leads to an increased secretion of an exoenzyme, such as an alpha-amylase, when compared with a cell with normal expression of the MrgA functional homologue cultivated under essentially identical conditions. In addition, the functional homologue of the MrgA protein shares an amino acid sequence identity with the MrgA protein of at least 50%, preferably 55%, 60%, 65%, 70%, 75%, 80%, 85%, 90%, 95%, 97%, or most preferably 99% when aligned as described above.

In the present context, the term "allelic variant" denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene. Allelic variants are included in the present definition of functional homologues.

The MrgA protein or functional homologue thereof may be a wild-type protein identified and isolated from a natural source. Such wild-type proteins may be specifically screened for by standard techniques known in the art. Furthermore, the MrgA protein or functional homologue thereof may be prepared by the DNA shuffling technique, such as described in J. E. Ness et al. Nature Biotechnology 17, 893-896 (1999). Moreover, the MrgA protein or functional homologue thereof may be an artificial variant. Such artificial variants may be constructed by standard techniques known in the art, such as by site-directed/random mutagenesis. In one embodiment of the invention, amino acid changes (in the artificial variant as well as in wild-type polypeptides) are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, AlaNal, Ser/Gly, Tyr/Phe, Ala/Pro, Lys/Arg, Asp/Asn, Leu/Ile, Leu/Val, Ala/Glu, and Asp/Gly as well as these in reverse.

It will be apparent to those skilled in the art that such modifications can be made outside the regions critical to the function of the molecule and still result in an active polypeptide. Amino acid residues essential to the activity of the polypeptide encoded by the nucleotide sequence of the invention, and therefore preferably not subject to modification, such as substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

Moreover, a nucleotide sequence encoding a polypeptide of the present invention may be modified by introduction of nucleotide substitutions which do not give rise to another amino acid sequence of the polypeptide encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods known in the art. Particularly useful is the procedure, which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used. For a general description of nucleotide substitution, see, e.g., Ford et al., 1991, Protein Expression and Purification 2: 95-107.

DETAILED DESCRIPTION OF THE INVENTION

The first aspect of the invention relates to a progeny cell derived from a parent cell, wherein
a) the progeny cell comprises at least one gene encoding MrgA protein or a functional homologue thereof and/or a DNA segment operably linked with the encoding gene, wherein said gene and/or DNA segment is manipulated with respect to the parent cell;
b) the progeny cell comprises two or more copies of a gene encoding MrgA protein or a functional homologue thereof; or
c) the progeny cell is mutated with respect to the parent cell;
whereby the progeny cell produces greater amounts of MrgA protein or a functional homologue thereof than the parent cell.

The cell of the invention produces greater amounts of MrgA protein or a funtional homologue thereof, than the parent cell. A comparison should be made by cultivating the cell of the invention as well as the parent cell under essentially identical conditions, and comparing the amount of MrgA protein by any standard method in the art. Preferably the cell of the invention produces at least 5% more MrgA than the parent, more preferably at least 10%, still more preferably at least 20%, and most preferably at least 50% more MrgA protein or a functional homologue thereof than the parent. Such overproduction may be accomplished by standard means known to the art, e.g., use of multicopy plasmids, multiple copies of the genes encoding MrgA or a functional homologue thereof, and/or the protein of interest, in the chromosome of the host, combined with altering the regulatory elements to increase expression, e.g., use of strong promoter(s), use of multiple promoters, use of enhancers, and so forth.

As the inventors show herein, a cell of the first aspect is capable of producing greater amounts of a protein of interest than the corresponding parent cell, when both are cultivated under essentially identical conditions.

Accordingly, a preferred embodiment of the invention relates to the cell of the first aspect, which produces greater amounts of a protein of interest than the parent cell. Preferably the protein of interest is an intracellular protein or an exoprotein. Preferably the cell of the invention secretes greater amounts of an exoprotein of interest than the parent cell. Preferably the cell of the invention secretes at least 5% more exoprotein than the parent, more preferably at least 10% more, still more preferably at least 20% more, and most preferably at least 50% more exoprotein than the parent. The amount of produced or secreted protein of interest from each cell may be determined by any suitable assay in the art; a non-limiting example is shown below with the determination of secreted amounts of the exoprotein alpha-amylase.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell. In one preferred embodiment, the bacterial host cell is a prokaryotic cell, preferably a Gram-positive prokaryotic cell, and more preferably the bacterial Gram positive cell is a species of the genus *Bacillus*, preferably selected from the group consisting of *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, and *Bacillus thuringiensis*.

A preferred embodiment relates to the cell of the invention, which is a bacterial cell, preferably a prokaryotic cell, more preferably a Gram-positive cell, and most preferably of the genus *Bacillus*; still more preferably it is of a species chosen from the group consisting of *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus stearothermophilus, Bacillus subtilis*, and *Bacillus thuringiensis*.

The protein of interest may be endogenous or exogenous to the host cell, it may be a homologous protein, or a heterologous protein.

A preferred embodiment relates to the cell, wherein said protein of interest is a protease, a lipase, a cutinase, an amylase, a galactosidase, a pullulanase, a cellulase, a glucose isomerase, a protein disulphide isomerase, a CGT'ase (cyclodextrin gluconotransferase), a phytase, a glucose oxidase, a glucosyl transferase, lactase, bilirubin oxidase, a xylanase, an antigenic microbial or protozoan protein, a bacterial protein toxin, a microbial surface protein, or a viral protein.

An evolutionary homologue of the MrgA protein, an allellic variant, an artificial variant, a shuffled variant, a species variant, and so forth, are all referred to as a "functional homologue" or the MrgA protein in the present description, and the inventors envision that such functional homologue protein(s) will be equally effective in the cell of the invention.

Specifically, a preferred embodiment relates to the cell, wherein the MrgA protein or functional homologue thereof comprises an amino acid sequence which is at least 70% identical to the amino acid sequence shown in SEQ ID NO:2, preferably at least 75%, 80%, 85%, 90%, 95%, 97%, or even 99% identical to the amino acid sequence shown in SEQ ID NO:2.

Another preferred embodiment relates to the cell of the invention, wherein the MrgA protein or functional homologue thereof comprises or consists of the amino acid sequence shown in SEQ ID NO:2.

Still another preferred embodiment relates to the cell of the invention, which comprises at least one exogenous copy of a polynucleotide encoding MrgA protein or a functional homologue thereof comprising an amino acid sequence which is at least 70% identical to the amino acid sequence shown in SEQ ID NO:2, preferably at least 75%, 80%, 85%, 90%, 95%, 97%, or even 99% identical to the amino acid sequence shown in SEQ ID NO:2.

In a preferred embodiment the cell of the invention comprises at least one exogenous copy of a polynucleotide encoding MrgA protein or a functional homologue thereof comprising or consisting of the amino acid sequence shown in SEQ ID NO:2.

A preferred cell comprises at least one exogenous copy of a polynucleotide, which:
 a) comprises a polynucleotide sequence which is at least 70% identical to the sequence shown in SEQ ID NO:1; preferably at least 75%, 80%, 85%, 90%, 95%, 97%, or even 99% identical to the sequence shown in SEQ ID NO:1; or
 b) hybridizes with the sequence shown in SEQ ID NO:1, under medium stringency conditions, preferably under medium-high stringency, and more preferably under high stringency conditions.

As described above, and exemplified herein, one preferred embodiment relates to a cell, wherein at least one exogenous copy of a gene encoding the MrgA protein or a functional homologue thereof is transcribed from one or more heterologous and/or artificial promoter.

In a preferred cell, at least one exogenous copy of a gene encoding the MrgA protein or a functional homologue thereof is integrated into the genome of the cell; or is present on an extra-chromosomal construct, preferably a plasmid.

Another aspect of the invention relates to a method for enhancing production of a protein of interest, the method comprising expressing said protein in a cell according to the first aspect.

Still another aspect of the invention relates to a method for producing a cell as defined in the first aspect, useful for production of a protein of interest, said method comprising a step of manipulating a cell to increase the expression of MrgA protein or functional homologue thereof.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, centrifugation, filtration, extraction, spray-drying, evaporation, precipitation, or extraction (see, e.g., Protein Purification, J.-C. Janson and Lars Ryden, editors, VCH Publishers, New York, 1989).

In a preferred embodiment of the method of the third aspect, the manipulated cell producess greater amounts of a protein of interest than the non-manipulated parent cell. Preferably the protein of interest is an intracellular protein or an exoprotein.

Another preferred embodiment relates to the method of the third aspect, wherein said method comprises the steps of:
 a) identifying a gene from the parent cell that encodes MrgA protein or a functional homologue thereof; and
 b) manipulating the cell to increase the expression of the gene identified in step (a), whereby the manipulated progeny cell expresses greater amounts of MrgA protein or functional homologue thereof, than the non-manipulated cell.

EXAMPLES

Materials and Methods

Strains
B. subtilis 168: F. Kunst et. al. "The complete genome sequence of the Gram-positive bacterium *Bacillus subtilis*". Nature (1997) 390:249-256.
B. subtilis AN53: B. subtilis 168 with plasmid pKTH10 and P920mrgA integrated in the amyE locus (this study).
B. subtilis AN36: B. subtilis 168 with plasmid p920mrgA integrated into the amyE locus (this study).
B. subtilis AN42: B. subtilis 168 with plasmid p740mrgA integrated into the amyE locus (this study).
B. subtilis AN50: B. subtilis 168 with plasmid p726mrgA integrated into the amyE locus (this study).
B. subtilis AN55: B. subtilis 168 with plasmid pKTH10 and P740mrgA integrated in the amyE locus (this study).
B. subtilis AN57: B. subtilis 168 with plasmid pKTH10 and P726mrgA integrated in the amyE locus (this study).
B. subtilis AN83: B. subtilis 168 with plasmid pKTH10 (this study).
B. subtilis AN214: B. subtilis 168 (pel::PconsBAN)
B. subtilis AN217: B. subtilis 168 (pel::PconsBAN; amyE::P726mrgA)
B. subtilis AN218: B. subtilis 168 (pel::PconsBAN; amyE::P740mrgA)
B. subtilis AN219: B. subtilis 168 (pel::PconsBAN; amyE::P920mrgA)

Competent cells were prepared and transformed as described by Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296-304.

Plasmids
pKTH10: Vehmaanpera J, Steinborn G, Hofemeister J.: "Genetic manipulation of *Bacillus amyloliquefaciens*." J. Biotechnol. 1991. 19(2-3):221-40. This plasmid constitutively express the *Bacillus amyloliquefaciens* alpha-amylase (AmyQ).

pDG268neo: This plasmid is a pDG268 derivative, which is unable to replicate in *Bacillus subtilis* (Antoniewski, C., Savelli, B., and Stragier, P., 1990, J. Bact 172). The plasmid contains the chloramphenicol (cam) resistance marker next to SfiI and BamHI restriction enzyme recognition sequences, flanked by the "5"' and "'3" portions of the amyE locus of *Bacillus subtilis*. This plasmid is used for introduction of the MrgA expression cassette and the cam marker into the amyE locus of *B. subtilis* via double homologous recombination cross-over. The sequence of pDG268neo is shown in SEQ ID NO: 3.

pAN213: This plasmid is a pDG268 derivative (Antoniewski, C., Savelli, B., and Stragier, P., 1990, J. Bact 172) which is unable to replicate in *Bacillus subtilis*. The plasmid contains the erythromycin resistance marker next to sacII and StyI restriction enzyme recognition sequences. All of this sequence is flanked by the "5"' and "'3" portions of the pectate lyase (pel) locus of *Bacillus subtilis* 168.

pAN213ban: The amyQ gene was amplified by PCR from the chromosome of *B. subtilis* by use of primers AN162 and AN163c. The upstream primer (AN162) encoded the synthetic promoter PconsBAN. The PCR product was cut with restriction enzymes sacII and MluI and ligated to the large SacII-MluI fragment of pAN213, resulting in plasmid pAN213ban. This plasmid is used for introduction of the AmyQ expression cassette and the erm marker into the pel locus of *B. subtilis* 168 via a double cross-over event. The sequence of pAN213ban is shown in SEQ ID NO: 16.

p920mrgA: The mrgA gene was amplified by PCR from the chromosome of *B. subtilis* by use of primers p920mrgaF2 (SEQ ID NO: 4) and MBmrgaR2 (SEQ ID NO: 5). The upstream primer (p920mrgaF2; SEQ ID NO: 4) comprised a synthetic constitutive promoter, P920 (SEQ ID NO: 6). The PCR product shown in SEQ ID NO: 7 was cut with restriction enzymes SfiI and BamHI and ligated to the large SfiI-BamHI fragment of pDG268neo, resulting in plasmid p920mrgA.

p740mrgA: The mrgA gene was amplified by PCR from the chromosome of *B. subtilis* by use of primers p740mrgaF2 (SEQ ID NO: 8) and MBmrgaR2 (SEQ ID NO: 5). The upstream primer (p740mrgaF2; SEQ ID NO: 8) comprised a synthetic constitutive promoter, P740 (SEQ ID NO: 9). The PCR product shown in SEQ ID NO: 10 was cut with restriction enzymes SfiI and BamHI and ligated to the large SfiI-BamHI fragment of pDG268neo, resulting in plasmid p740mrgA.

p726mrgA: The mrgA was amplified by PCR from the chromosome of *B. subtilis* by use of primers p726mrgaF2 (SEQ ID NO: 11) and MBmrgaR2 (SEQ ID NO: 5). The upstream primer (p726mrgaF2; SEQ ID NO: 11) comprised the constitutive synthetic promoter P726 (SEQ ID NO: 12). The PCR product shown in SEQ ID NO: 13 was cut with restriction enzymes SfiI and BamHI and ligated to the large SfiI-BamHI fragment of pDG268neo, resulting in plasmid p726mrgA.

Primers:

P920mrgaF (SEQ ID NO: 4):
ctgaggccaattaggccaagtttattcttgacattagggaacatgcatga tataataggtaaagtaaacagatcacaaggaggacgttatc P740mrgaF (SEQ ID NO: 8):
ctgaggccaattaggcccggaagtttgttgacacagctccaggatacaaa tataatgggtcgactaaacagatcacaaggaggacgttatc P726mrgaF (SEQ ID NO: 11):
ctgaggccaattaggccgaggtgagatttgacactagtaggctacgggac tataatgcgggaagtaaacagatcacaaggaggacgttatc MBmrgaR2 (SEQ ID NO: 5):
tgaaggatccacgcgtccagcagacagaaagcag AN162 (SEQ ID NO: 14):
agactgtccgcggtgtaaaaaataggaataaagggggggttgacattattt tactgatatgtataatataatttgtataagaaaatgag AN163c (SEQ ID NO: 15):
gcatacacgcgttgtcacacctgatgccgacc General Molecular Biology Methods Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for *Bacillus*". John Wiley and Sons, 1990).

Enzymes for DNA manipulations were used according to the specifications of the suppliers (e.g. restriction endonucleases, ligases etc. are obtainable from New England Biolabs, Inc.).

Media

LB agar (as described in Ausubel, F. M. et al. (eds.) "Current protocols in Molecular Biology". John Wiley and Sons, 1995).

LBP is LB agar supplemented with 0.05 M potassium phosphate, pH 7.0

LBPG is LB agar supplemented with 0.5% Glucose and 0.05 M potassium phosphate, pH 7.0.

LBPSK is LB agar supplemented with 0.05 M potassium phosphate, pH 7.0 and 1% of skimmed milk.

BPX media is described in EP 0 506 780 (WO 91/09129).

Fermentations

Fermentations to evaluate the amylase yields were performed in shakeflasks with 100 ml BPX at 37° C., 300 rpm for seven days. Culture volumes of 10 ml were harvested and centrifuged at 10.000 g to remove cells and debris. The clear supernants were used for assaying alpha-amylase activity.

Assay for Alpha-Amylase Activity

Alpha-amylase activity was determined by a method employing an enzymatic colorimetric test with 4,6-ethylidene($G_7$)-p-nitrophenyl($G_1$)-alpha,D-maltoheptaoside (ethylidene-$G_7$PNP) as substrate (Boehringer Mannheim, Germany art. 1442309). Under a specified set of conditions (temp., pH, reaction time, buffer conditions) 1 mg of a given a-amylase will hydrolyse a certain amount of substrate and a yellow colour will be produced. The colour intensity is measured at 405 nm. The measured absorbance is directly proportional to the activity of the alpha-amylase in question under a given set of conditions.

Example 1

The mrgA gene was amplified by PCR from the chromosome of *B. subtilis* by use of primers p920mrgaF2 (SEQ ID NO: 4) and MBmrgaR2 (SEQ ID NO: 5). The upstream primer (p920mrgaF2) comprised the constitutive synthetic promoter P920 (SEQ ID NO:6). The PCR product (SEQ ID NO: 7) was cut with restriction enzymes SfiI and BamHI and ligated to the large SfiI-BamHI fragment of pDG268neo, resulting in plasmid p920mrgA. The ligation-mixture of p920mrgA, described in the Material and Methods section, was introduced by transformation into the B. subtilis 168 strain, and the transformants were plated on LBPSK media supplemented with 6 microg/ml chloramphenicol to select for integrants. Transformants growing on these plates have integrated the plasmid in the amy locus, either by a single (Cam$^+$kan$^+$) or double cross-over event (cam$^+$kan$^-$). Transformants were re-streaked on LBPSK/cam media with and without 20 microg/ml kanamycine. Strains where double cross-over events had occurred were cam$^+$kan$^-$. These strains no longer showed the tell-tale clearing zones; which signified that that integration in, and disruption of, the amy gene, had taken place. The site of integration was verified by PCR, the integrated copy of mrgA was verified by sequence analysis, and the strain was named AN36. AN36 was transformed with plasmid pKTH10 which constitutively expresses the alpha-amylase AmyQ of Bacillus amyloliquefaciens. The resulting strain was named AN53. Yields of amylase from AN53 were determined in triplicate from three independent isolates, and compared to the yield of amylase from the control strain AN83. Results are shown in table 1; the AN53 strain constitutively expressing mrgA from the synthetic promoter has an increased alpha-amylase yield, which on average is 13% higher than the control strain, AN83, which only comprises a wild-type copy of the mrgA gene.

TABLE 1

Yields of amylase from AN53 were determined in triplicate from three independent isolates, and compared to the yield of amylase from the control strain AN83. The average yields of each strain are also shown.

| Strain | Amylase activity (relative) | average | average (in %) |
|---|---|---|---|
| AN53-1.1 | 15.7 | 13.5 | 113% |
| AN53-1.2 | 15.8 | | |
| AN53-1.3 | 14.9 | | |
| AN53-2.1 | 12.5 | | |
| AN53-2.2 | 8.65 | | |
| AN53-2.3 | Nd | | |
| AN53-3.1 | Nd | | |
| AN53-3.2 | Nd | | |
| AN53-3.3 | Nd | | |
| AN83-1.1 | 10.6 | 11.9 | 100% |
| AN83-1.2 | 15.7 | | |
| AN83-1.3 | 13.8 | | |
| AN83-2.1 | 8.7 | | |
| AN83-2.2 | 7.72 | | |
| AN83-2.3 | 10.1 | | |
| AN83-3.1 | 14.1 | | |
| AN83-3.2 | Nd | | |
| AN83-3.3 | 14.6 | | |

Nd: Not determined.

Example 2

The mrgA gene was amplified by PCR from the chromosome of B. subtilis by use of primers p740mrgaF2 (SEQ ID NO: 8) and MBmrgaR2 (SEQ ID NO: 5). The upstream primer (p740mrgaF2) comprised the constitutive synthetic promoter P740 (SEQ ID NO: 9). The PCR product (SEQ ID NO: 10) was cut with restriction enzymes SfiI and BamHI, and ligated to the large SfiI-BamHI fragment of pDG268neo, resulting in plasmid p740mrgA. The ligation-mixture of p740mrgA, described in the Material and Methods section, was introduced by transformation into the B. subtilis 168 strain, and the transformants were plated on LBPSK media supplemented with 6 microg/ml chloramphenicol (cam) to select for integrants. Transformants growing on these plates have integrated the plasmid in the amy locus, either by a single (Cam$^+$kan$^+$) or double cross-over event (cam$^+$kan$^-$). The transformants were re-streaked on LBPSK/cam media with and without 20 microg/ml kanamycine. Strains where double cross-over events had occurred were cam$^+$kan$^-$. These strains no longer showed the tell-tale clearing zones; which signified that that integration in, and disruption of, the amy gene, had taken place. The site of integration was verified by PCR, the integrated copy of mrgA was verified by sequence analysis, and the strain was named AN42. AN42 was transformed with plasmid pKTH10 which constitutively express the alpha-amylase AmyQ of Bacillus amyloliquefaciens. The resulting strain was named AN55. Yields of amylase from AN55 were determined in triplicate from three independent isolates, and compared to yield of amylase from the control strain AN83. Results are shown in table 2; the AN55 strain constitutively expressing mrgA from the synthetic promoter has an increased alpha-amylase yield, which on average is 21% higher than the control strain, AN83, which only comprises a wild-type copy of the mrgA gene.

TABLE 2

Yields of amylase from AN55 were determined in triplicate from three independent isolates, and compared to the yield of amylase from the control strain AN83. The average yields of each strain are also shown.

| Strain | Amylase activity (relative) | average | average (in %) |
|---|---|---|---|
| AN55-1.1 | 11.5 | 14.4 | 121% |
| AN55-1.2 | 10.8 | | |
| AN55-1.3 | 13.3 | | |
| AN55-2.1 | 17.4 | | |
| AN55-2.2 | 17.3 | | |
| AN55-2.3 | 15.6 | | |
| AN55-3.1 | 11.2 | | |
| AN55-3.2 | 14.8 | | |
| AN55-3.3 | 18.1 | | |
| AN83-1.1 | 10.6 | 11.9 | 100% |
| AN83-1.2 | 15.7 | | |
| AN83-1.3 | 13.8 | | |
| AN83-2.1 | 8.7 | | |
| AN83-2.2 | 7.72 | | |
| AN83-2.3 | 10.1 | | |
| AN83-3.1 | 14.1 | | |
| AN83-3.2 | Nd | | |
| AN83-3.3 | 14.6 | | |

Nd: Not determined.

Example 3

The mrgA gene was amplified by PCR from the chromosome of B. subtilis by use of primers p726mrgaF2 (SEQ ID NO: 11) and MBmrgaR2 (SEQ ID NO: 5). The upstream primer (p726mrgaF2) comprised the constitutive synthetic promoter P726 (SEQ ID NO: 12). The PCR product (SEQ ID NO: 13) was cut with restriction enzymes SfiI and BamHI and ligated to the large SfiI-BamHI fragment of pDG268neo, resulting in plasmid p726mrgA. The ligation-mixture of p726mrgA, described in the Material and Methods section, was introduced by transformation into the B. subtilis 168 strain, and the transformants were plated on LBPSK media supplemented with 6 microg/ml chloramphenicol to select for integrants. Transformants growing on these plates have integrated the plasmid in the amy locus, either by a single (Cam$^+$kan$^+$) or double cross-over event (cam$^+$kan$^-$). The transformants were then re-streaked on LBPSK/cam media with and without 20 microg/ml kanamycine. Strains where double cross-over events had occurred were cam$^+$kan$^-$. These strains no longer showed the tell-tale clearing zones; which signified that that integration in, and disruption of, the amy gene, had taken place. The site of integration was verified by PCR, the integrated copy of mrgA was verified by sequence analysis, and the strain was named AN50. AN50 was then transformed with plasmid pKTH10, which constitutively express the alpha-amylase AmyQ of Bacillus amyloliquefaciens. The resulting strain was named AN57. Yields of amylase from AN57 were determined in triplicate from three independent isolates, and compared to the yield of amylase from the control strain AN83. Results are shown in table 3; the AN55 strain constitutively expressing mrgA from the synthetic promoter has an increased alpha-amylase yield, which on average is 40% higher than the control strain, AN83, which only comprises a wild-type copy of the mrgA gene.

TABLE 3

Yields of amylase from AN57 were determined in triplicate from three independent isolates, and compared to the yield of amylase from the control strain AN83. The average yields of each strain are also shown.

| Strain | Amylase activity (relative) | average | average (in %) |
|---|---|---|---|
| AN57-1.1 | 15.5 | 16.6 | 140% |
| AN57-1.2 | 10.6 | | |
| AN57-1.3 | 17.3 | | |
| AN57-2.1 | 17.4 | | |
| AN57-2.2 | 20.7 | | |
| AN57-2.3 | 13.9 | | |
| AN57-3.1 | 15.1 | | |
| AN57-3.2 | 17 | | |
| AN57-3.3 | 22 | | |
| AN83-1.1 | 10.6 | 11.9 | 100% |
| AN83-1.2 | 15.7 | | |
| AN83-1.3 | 13.8 | | |
| AN83-2.1 | 8.7 | | |
| AN83-2.2 | 7.72 | | |
| AN83-2.3 | 10.1 | | |
| AN83-3.1 | 14.1 | | |
| AN83-3.2 | Nd | | |
| AN83-3.3 | 14.6 | | |

Nd: Not determined.

Example 4 pAN213ban, described in the Material and Methods section, was introduced by transformation into the B. subtilis 168 strain and plated on LBPGS media supplemented with microgram/ml erythromycin to select for integrants. Transformants on these plates have integrated the plasmid in the pel locus, either by a single (erm⁺kan⁺) or double cross-over event (erm⁺kan⁻). Transformants were re-streaked on LBPGS/erm media with and without 20 microgram/ml kanamycine. Strains where double cross-over events occurred were scored as erm⁺kan⁻. These strains showed larger than wildtype clearing zones as an indication of $P_{consBAN}$-amyQ integration and expression. The site of integration was verified by PCR. The resulting strain was named AN214. AN50 was transformed with chromosomal DNA from AN214 and transformants with the genotype (pel::$P_{cons}$BAN, erm; amyE::P726mrgA, cam) were scored on plates. The resulting strain was verified by PCR and named AN217. Yield of amylase from AN217 was determined in duplicate from four independent isolates and compared to yield of amylase from the control strain AN214 (table 4).

TABLE 4

Yield of amylase from AN217 determined in duplicates from four independent isolates and compared to yield of amylase from the control strain AN214.

| Strain | Amylase activity (relative) | average | |
|---|---|---|---|
| AN214-1.1 | 10.5 | 14.0 | 100% |
| AN214-1.2 | 10.9 | | |
| AN214-2.1 | 14.5 | | |
| AN214-2.2 | 13.6 | | |
| AN214-3.1 | 14.6 | | |
| AN214-3.2 | 16.1 | | |
| AN214-4.1 | 14.1 | | |
| AN214-4.2 | 17.9 | | |
| AN217-1.1 | 17.1 | 16.7 | 119% |
| AN217-1.2 | 16.5 | | |
| AN217-2.1 | 14.9 | | |
| AN217-2.2 | 14.6 | | |
| AN217-3.1 | 19.1 | | |
| AN217-3.2 | 18.1 | | |
| AN217-4.1 | 16.2 | | |
| AN217-4.2 | 17.2 | | |

Example 5

AN36 was transformed with chromosomal DNA from AN214 and transformants with the genotype (pek:$P_{cons}$BAN, erm; amyE::P920mrgA, cam) were scored on plates. The resulting strain was verified by PCR and named AN219. AN42 were transformed with chromosomal DNA from AN214 and transformants with the genotype (pek:$P_{cons}$BAN, erm; amyE::P740mrgA, cam) were scored on plates. The resulting strain was verified by PCR and named AN218. Yield of amylase from AN214, AN218 and AN219 were determined in duplicate from four independent isolates of each strain (table 5).

TABLE 5

Relative average yields of amylase from AN214, AN218 and AN219, determined in duplicate from four independent isolates of each strain.

| Strain | Amylase activity |
|---|---|
| AN214 | 100 |
| AN218 | 107 |
| AN219 | 106 |

The invention claimed is:

1. A progeny *Bacillus* cell derived from a parent cell, wherein the cell comprises a nucleic acid construct encoding a heterologous exoprotein of interest and:
   a) a heterologous promoter operably linked with at least one gene encoding a metallo regulated gene A (MrgA) protein with an amino acid sequence having at least 95% sequence identity to SEQ ID NO:2; or
   b) at least one heterologous gene encoding MrgA protein with an amino acid sequence having at least 95% sequence identity to SEQ ID NO:2, wherein the secretion of the heterologous exoprotein and MrgA is increased compared to an otherwise isogenic *Bacillus* cell without a) or b), and wherein the exoprotein is not galactosidase.

2. The cell of claim 1, wherein the *Bacillus* cell is of a species selected from the group consisting of *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus stearothermophilus, Bacillus subtilis,* and *Bacillus thuringiensis*.

3. The cell of claim 1, wherein said exoprotein is a protease, a lipase, a cutinase, an amylase, a pullulanase, a cellulase, a glucose isomerase, a protein disulphide isomerase, a cyclodextrin gluconotransferase, a phytase, a glucose oxidase, a glucosyl transferase, lactase, bilirubin oxidase, a xylanase, an antigenic microbial or protozoan protein, a bacterial protein toxin, a microbial surface protein, or a viral protein.

4. The cell of claim 1, wherein the MrgA protein comprises an amino acid sequence having at least 97% sequence identity to SEQ ID NO: 2.

5. The cell of claim 1, wherein the MrgA protein comprises SEQ ID NO: 2.

6. The cell of claim 1, wherein said cell comprises at least one exogenous copy of a polynucleotide encoding an MrgA protein comprising an amino acid sequence having at least 95% sequence identity to SEQ ID NO: 2.

7. The cell of claim 1, wherein said cell comprises at least one exogenous copy of a polynucleotide encoding MrgA protein comprising SEQ ID NO: 2.

8. The cell of claim 1, which comprises at least one exogenous copy of a polynucleotide, which:
   a) comprises a polynucleotide sequence having at least 97% sequence identity to SEQ ID NO: 1; or
   b) hybridizes with the sequence shown in SEQ ID NO: 1, under high stringency conditions.

9. The cell of claim 1, wherein said cell comprises at least one exogenous copy of a gene encoding the MrgA protein transcribed from one or more heterologous promoters or artificial promoters.

10. The cell of claim 1, wherein said cell comprises at least one exogenous copy of a gene encoding the MrgA protein integrated into the genome of the cell.

11. The cell of claim 1, wherein said cell comprises at least one exogenous copy of a gene encoding the MrgA protein present on an extra-chromosomal construct.

* * * * *

SEQUENCE LISTING

<160> NUMBER OF SEQ ID NOS: 16

<210> SEQ ID NO 1
<211> LENGTH: 815
<212> TYPE: DNA
<213> ORGANISM: Bacillus subtilis 168

```
<220> FEATURE:
<221> NAME/KEY: misc_feature
<222> LOCATION: (201)..(659)
<223> OTHER INFORMATION: MrgA encoding sequence

<400> SEQUENCE: 1
aagaatttgc gatacccgat cggaaagggc atcaagctca ccctgctgtt ccgatcgctt      60
tttccttggt ctgcgtggga gtctatcctg aagaaaaagc tattcagctg atctaaatta    120
taattattat aatttagtat tgattttat ttagtatatg atataattaa gtcaacagat     180
cacaaggagg acgttatctt atgaaaactg aaaacgcaaa aacaaatcaa acattagttg    240
agaattcact gaacacacaa ttatcaaact ggtttctttt atactctaag ctccaccgtt    300
tccattggta tgtgaaaggg cctcatttct ttacattgca cgagaaattt gaagaacttt    360
atgaccatgc ggctgaaaca gtggatacca tcgctgagcg cctgctggcg attggcggac    420
agcctgttgc cacagtgaaa gaatacactg agcatgcatc tatcacagac ggcggaaacg    480
aaacatcagc atcagaaatg gtacaagcat tggtaaacga ctacaaacaa atcagcagcg    540
aatctaaatt cgtgatcggc ctggctgaag aaaatcaaga caatgcgaca gcggacttgt    600
ttgtcggatt aattgaagaa gttgaaaaac aagtgtggat gctttcctct tatttagggt    660
aacaaaaaag ctgaacctta atcgggttca gcttttgtt ttttcttagc ttgaactgct      720
ttctgtctgc ttggtcagtg ttgcgttcaa cgttttcgtt tttcccttc gcagcacttg    780 gattgttgtt ttatctccga cttttaagtc tttgt                                 815

<210> SEQ ID NO 2
<211> LENGTH: 153
<212> TYPE: PRT
<213> ORGANISM: Bacillus subtilis 168
<220> FEATURE:
<221> NAME/KEY: PEPTIDE
<222> LOCATION: (1)..(153)
<223> OTHER INFORMATION: MrgA protein

<400> SEQUENCE: 2

Met Lys Thr Glu Asn Ala Lys Thr Asn Gln Thr Leu Val Glu Asn Ser
1               5                   10                  15

Leu Asn Thr Gln Leu Ser Asn Trp Phe Leu Leu Tyr Ser Lys Leu His
            20                  25                  30

Arg Phe His Trp Tyr Val Lys Gly Pro His Phe Phe Thr Leu His Glu
        35                  40                  45

Lys Phe Glu Glu Leu Tyr Asp His Ala Ala Glu Thr Val Asp Thr Ile
    50                  55                  60

Ala Glu Arg Leu Leu Ala Ile Gly Gly Gln Pro Val Ala Thr Val Lys
65                  70                  75                  80

Glu Tyr Thr Glu His Ala Ser Ile Thr Asp Gly Gly Asn Glu Thr Ser
                85                  90                  95

Ala Ser Glu Met Val Gln Ala Leu Val Asn Asp Tyr Lys Gln Ile Ser
            100                 105                 110

Ser Glu Ser Lys Phe Val Ile Gly Leu Ala Glu Glu Asn Gln Asp Asn
        115                 120                 125

Ala Thr Ala Asp Leu Phe Val Gly Leu Ile Glu Glu Val Glu Lys Gln
    130                 135                 140

Val Trp Met Leu Ser Ser Tyr Leu Gly
145                 150

<210> SEQ ID NO 3
<211> LENGTH: 8644
```

<212> TYPE: DNA
<213> ORGANISM: Artificial sequence
<220> FEATURE:
<223> OTHER INFORMATION: Plasmid pDG268neo

<400> SEQUENCE: 3

| | | | | | |
|---|---|---|---|---|---|
| aacaaaattc | tccagtcttc | acatcggttt | gaaaggagga | agcggaagaa | tgaagtaaga | 60 |
| gggattttg | actccgaagt | aagtcttcaa | aaatcaaat | aaggagtgtc | aagaatgttt | 120 |
| gcaaaacgat | tcaaaacctc | tttactgccg | ttattcgctg | gattttatt | gctgtttcat | 180 |
| ttggttctgg | caggaccggc | ggctgcgagt | gctgaaacgg | cgaacaaatc | gaatgagctt | 240 |
| acagcaccgt | cgatcaaaag | cggaaccatt | cttcatgcat | ggaattggtc | gttcaatacg | 300 |
| ttaaaacaca | atatgaagga | tattcatgat | gcaggatata | cagccattca | gacatctccg | 360 |
| attaaccaag | taaggaagg | gaatcaagga | gataaaagca | tgtcgaactg | gtactggctg | 420 |
| tatcagccga | catcgtatca | aattggcaac | cgttacttag | gtactgaaca | agaatttaaa | 480 |
| gaaatgtgtg | cagccgctga | agaatatggc | ataaggtca | ttgttgacgc | gcggccgcgg | 540 |
| atccatacac | aaaaaaacgc | tgtgcccttt | aaccgcacag | cgttttttta | ttgattaacg | 600 |
| cgttgccgct | tctgcgttaa | caagtccgct | tccatacaag | ttcgtgcttc | ctaaactagt | 660 |
| tgccgtattc | tttagatgat | ttcgaatttg | tacattagac | caagatgggt | tcttttgttt | 720 |
| aacaagggcg | gccgcacctg | caacatgagg | agtagccatc | gatgtaccgt | ttaagctggc | 780 |
| atatgttgaa | cctgggtatg | tgctctgcac | gtttaccccg | ggtgcgacaa | tgtcaaggcc | 840 |
| tgcgccatac | tgtgaaaagc | tagcgcggtt | gttgttttga | tcagtagctc | cgactgccat | 900 |
| tgcgttcgca | tagcgcgccg | gatagctgat | tgagcctgca | cctgaattcc | cagatgccgc | 960 |
| tacaacaaga | acgcctctag | aagtcgcgct | attaacagct | tgctcgagtg | tggcacttgg | 1020 |
| cgaagggctt | cctaaactca | aattagcaac | gtgcatgcca | ttgttccctg | cccattccaa | 1080 |
| tccttgggca | atcgagctga | ccgaacctga | accgctcgcc | cctaggactt | taacagcgta | 1140 |
| tagctcagcg | ctcggcgcta | cgccaagaac | gccaatcgaa | ttgtttaaag | cagcgatcgt | 1200 |
| cccggccaca | tgcgtgccat | gcccattccc | atcttgagtc | gacggttccc | ctggtacaaa | 1260 |
| gcttgcgcca | ccacgaatat | ttagatctgg | atgagtggat | atccctgtat | cgaggacagc | 1320 |
| aacttttaca | ccagaacctg | tcaatccacg | gttatgggca | gctggggctt | gcacacggct | 1380 |
| aattccccat | ggtaccgatt | gcgccattgt | cgttacttct | gcatcctctt | caatataaga | 1440 |
| aatcgctgga | tcgagttcaa | gcgcgtccac | atcttctggg | cttaactcaa | cggataaaac | 1500 |
| aggaatcgtt | tcaaattcat | gaagcaattc | aatttcgact | tcctcttcct | cagagagaat | 1560 |
| ggcgacctcg | tcatttgcct | ctacttgttc | tacaaactca | ctgacagctt | cctgctcatt | 1620 |
| aaagccaatt | aaatattttt | cttttgcttc | ttcagcagcc | gatgcgatcg | atgaactaaa | 1680 |
| agcaacagaa | atgagtagtg | cggtgcttgc | gacaattttc | cccaacggtt | tcttcattcg | 1740 |
| gtttccctcc | tcatttttat | agagctccat | aatacataat | tttcaaactg | ataaaatgat | 1800 |
| ttttcataaa | tccattagac | ggtgcaaata | tatgtttta | atgttcttcg | tttttaggca | 1860 |
| tccctccttt | caagataaat | aatttataca | ctattctatt | ggaatcttaa | tcattccaat | 1920 |
| agaaaaatat | gtaatgatta | taaataagtc | gcttcttatc | ataaatatat | ttacatattc | 1980 |
| atttaatact | acatcatgtt | aggtatagta | aggctatcaa | gggtgtctta | atttctactt | 2040 |
| gtaacaatgt | attggcatat | tatatattga | attgagaaaa | ttaaatacag | cgataattca | 2100 |
| catgaacaag | ttcattggta | gttatatttt | caaattttca | aggttgtgct | tgtatgtcat | 2160 |
| tctatagtta | gataagcatt | tgaggtagag | tccgtccgaa | tatatttgta | atctgaagaa | 2220 |

```
ggttcaaaca tatttctata taacgtattc ttttttttgta gttcttactt ttgaggggcg   2280
ttacaattca aagatattat ctttaattaa gcttaacatt aataattctt caattgcaac   2340
aaaaaaagca cttttatcta aggtttcatc ttacgtttcg agggcccctc cattttctta   2400
tacaaattat attatacata tcagtaaaat aatgtcaacc cccctttatt cctttttttt   2460
acacagcgga cagtctggac agcaggccct taaggccaat tctcatgttt gacagcttat   2520
catcggcaat agttacccTT attatcaaga taagaaagaa aaggattttt cgctacgctc   2580
aaatccttta aaaaaacaca aaagaccaca ttttttaatg tggtctttat tcttcaacta   2640
aagcacccat tagttcaaca aacgaaaatt ggataaagtg ggatatttTT aaaatatata   2700
tttatgttac agtaatattg acttttaaaa aaggattgat tctaatgaag aaagcagaca   2760
agtaagcctc ctaaattcac tttagataaa aatttaggag gcatatcaaa tgaactttaa   2820
taaaattgat ttagacaatt ggaagagaaa agagatattt aatcattatt tgaaccaaca   2880
aacgactttt agtataacca cagaaattga tattagtgtt ttataccgaa acataaaaca   2940
agaaggatat aaattttacc ctgcatttat tttcttagtg acaagggtga taaactcaaa   3000
tacagctttt agaactggtt acaatagcga cggagagtta ggttattggg ataagttaga   3060
gccactttat acaattttTG atggtgtatc taaaacattc tctggtattt ggactcctgt   3120
aaagaatgac ttcaaagagt tttatgattT ataccttTCT gatgtagaga aatataatgg   3180
ttcggggaaa ttgtttccca aaacacctat acctgaaaat gcttttTCTC tttctattat   3240
tccatggact tcatttactg ggtttaactT aaatatcaat aataatagta attaccttct   3300
acccattatt acagcaggaa aattcattaa taaaggtaat tcaatatatt taccgctatc   3360
tttacaggta catcattctg tttgtgatgg ttatcatgca ggattgttta tgaactctat   3420
tcaggaattg tcagataggc ctaatgactg gctttTATAA tatgagataa tgccgactgt   3480
acttttTACA gtcggttTTC taatgtcact aacctgcccc gttagttgaa gaaggttttt   3540
atattacagc tccagatcct ctacgccgga cgcatcgtgg ccggcatcac cggcgccaca   3600
ggtgcggttg ctggcgccta tcgccgac atcaccgatg gggaagatcg ggctcgccac   3660
ttcgggctca tgagcgcttg tttcggcgtg ggtatggtgg caggccccgt ggccggggga   3720
ctgttgggcg ccatctcctt gcatgcacca ttccttgcgg cggcggtgct caacggcctc   3780
aacctactac tgggctgctt cctaatgcag gagtcgcata agggagagcg tcgacatgga   3840
tgagcgatga tgatatccgt ttaggctggg cggtgatagc ttctcgttca ggcagtacgc   3900
ctcttttctt ttccagacct gagggaggcg gaaatggtgt gaggttcccg gggaaaagcc   3960
aaataggcga tcgcgggagt gctttatttg aagatcaggc tatcactgcg gtcaatagat   4020
ttcacaatgt gatggctgga cagcctgagg aactctcgaa cccgaatgga aacaaccaga   4080
tatttatgaa tcagcgcggc tcacatggcg ttgtgctggc aaatgcaggt tcatcctctg   4140
tctctatcaa tacggcaaca aaattgcctg atggcaggta tgacaataaa gctggagcgg   4200
gttcatttca agtgaacgat ggtaaactga caggcacgat caatgccagg tctgtagctg   4260
tgctttatcc tgatgatatt gcaaaagcgc ctcatgtttt ccttgagaat tacaaaacag   4320
gtgtaacaca ttctttcaat gatcaactga cgattaccTT gcgtgcagat gcgaatacaa   4380
caaaagccgt ttatcaaatc aataatggac cagacgacag gcgtttaagg atggagatca   4440
attcacaatc ggaaaaggag atccaattTG gcaaaacata caccatcatg ttaaaaggaa   4500
cgaacagtga tggtgtaacg aggaccgaga aatacagttg tgttaaaaga gatccagcgt   4560
cggccaaaac catcggctat caaaatccga atcattggag ccaggtaaat gcttatatct   4620
```

```
ataaacatga tgggagccga gtaattgaat tgaccggatc ttggcctgga aaaccaatga   4680
ctaaaaatgc agacggaatt tacacgctga cgctgcctgc ggacacggat acaaccaacg   4740
caaaagtgat tttaataat ggcagcgccc aagtgcccgg tcagaatcag cctggctttg    4800
attacgtgct aaatggttta tataatgact cgggcttaag cggttctctt ccccattgag   4860
ggcaaggcta gacgggactt accgaaagaa accatcaatg atggtttctt ttttgttcat   4920
aaatcagaca aaacttttct cttgcaaaag tttgtgaagt gttgcacaat ataaatgtga   4980
aatacttcac aaacaaaaag acatcaaaga gaaacatacc ctgcaaggat gctgatattg   5040
tctgcatttg cgccggagca aaccaaaaac ctggtgagac acgccttgaa ttagtagaaa   5100
agaacttgaa gattttcaaa ggcatcgtta gtgaagtcat ggcgagcgga tttgacggca   5160
ttttcttagt cggtaacaat cctcgttaaa ggacaaggac ctgagcggaa gtgtatcgta   5220
cagtagacgg agtatactag tatagtctat agtccgtgga attattatat ttatctccga   5280
cgatattctc atcagtgaaa tccagctgga gttctttagc aaattttttt attagctgaa   5340
cttagtatta gtggggccgc tgataattac taatactagg agaagttaat aaatacgtaa   5400
ccaacatgat taacaattat tagaggtcat cgttcaaaat ggtatgcgtt ttgacacatc   5460
cactatatat ccgtgtcgtt ctgtccactc ctgaatccca ttccagaaat tctctagcga   5520
ttccagaagt ttctcagagt cggaaagttg accagacatt acgaactggc acagatggtc   5580
ataacctgaa ggaagatctg attgcttaac tgcttcagtt aagaccgaag cgctcgtcgt   5640
ataacagatg cgatgatgca gaccaatcaa catggcacct gccattgcta cctgtacagt   5700
caaggatggt agaaatgttg tcggtccttg cacacgaata ttacgccatt tgcctgcata   5760
ttcaaacagc tcttctacga taagggcaca aatcgcatcg tggaacgttt gggcttctac   5820
cgatttagca gtttgataca ctttctctaa gtatccacct gaatcataaa tcggcaaaat   5880
agagaaaaat tgaccatgtg taagcggcca atctgattcc acctgagatg cataatctag   5940
tagaatctct tcgctatcaa aattcacttc caccttccac tcaccggttg tccattcatg   6000
gctgaactct gcttcctctg ttgacatgac acacatcatc tcaatatccg aatagggccc   6060
atcagtctga cgaccaagag agccataaac accaatagcc ttaacatcat ccccatattt   6120
atccaatatt cgttccttaa tttcatgaac aatcttcatt ctttcttctc tagtcattat   6180
tattggtcca ttcactattc tcattccctt ttcagataat tttagatttg cttttctaaa   6240
taagaatatt tggagagcac cgttcttatt cagctattaa taactcgtct tcctaagcat   6300
catggtctca cttttccact ttttgtcttg tccactaaaa cccttgattt ttcatctgaa   6360
taaatgctac tattaggaca cataatatta aaagaaaccc ccatctattt agttatttgt   6420
ttagtcactt ataactttaa cagatggggt ttttctgtgc aaccaatttt aagggttttc   6480
aatactttaa aacacataca taccaacact tcaacgcacc tttcagcaac taaaataaaa   6540
atgacgttat ttctatatgt atcaagataa gaaagaacaa gttcaaaacc atcaaaaaaa   6600
gacacctttt caggtgcttt ttttatttta taaactcatt ccctgatctc cccatactcc   6660
tccaatccaa agctatttag aaagattact atatcctcaa acaggcggta accggcctct   6720
tcatcgggaa tgcgcgcgac cttcagcatc gccggcatgt cccccctggcg gacgggaagt   6780 atccagctcg aggtcgggcc gcgttgctgg cgttttttcca taggctccgc cccctgacg    6840 agcatcacaa aaatcgacgc tcaagtcaga ggtggcgaaa cccgacagga ctataaagat   6900
accaggcgtt tcccctgga agctccctcg tgcgctctcc tgttccgacc ctgccgctta    6960
ccggatacct gtccgccttt ctcccttcgg gaagcgtggc gctttctcat agctcacgct   7020
```

```
gtaggtatct cagttcggtg taggtcgttc gctccaagct gggctgtgtg cacgaacccc    7080
ccgttcagcc cgaccgctgc gccttatccg gtaactatcg tcttgagtcc aacccggtaa    7140
gacacgactt atcgccactg gcagcagcca ctggtaacag gattagcaga gcgaggtatg    7200
taggcggtgc tacagagttc ttgaagtggt ggcctaacta cggctacact agaaggacag    7260
tatttggtat ctgcgctctg ctgaagccag ttaccttcgg aaaaagagtt ggtagctctt    7320
gatccggcaa acaaaccacc gctggtagcg gtggtttttt tgtttgcaag cagcagatta    7380
cgcgcagaaa aaaaggatct caagaagatc ctttgatctt ttctacgggg tctgacgctc    7440
agtggaacga aaactcacgt taagggattt tggtcatgag attatcaaaa aggatcttca    7500
cctagatcct tttaaattaa aaatgaagtt ttaaatcaat ctaaagtata tatgagtaaa    7560
cttggtctga cagttaccaa tgcttaatca gtgaggcacc tatctcagcg atctgtctat    7620
ttcgttcatc catagttgcc tgactccccg tcgtgtagat aactacgata cgggagggct    7680
taccatctgg ccccagtgct gcaatgatac cgcgagaccc acgctcaccg gctccagatt    7740
tatcagcaat aaaccagcca gccggaaggg ccgagcgcag aagtggtcct gcaactttat    7800
ccgcctccat ccagtctatt aattgttgcc gggaagctag agtaagtagt tcgccagtta    7860
atagtttgcg caacgttgtt gccattgctg caggcatcgt ggtgtcacgc tcgtcgtttg    7920
gtatggcttc attcagctcc ggttcccaac gatcaaggcg agttacatga tcccccatgt    7980
tgtgcaaaaa agcggttagc tccttcggtc ctccgatcgt tgtcagaagt aagttggccg    8040
cagtgttatc actcatggtt atggcagcac tgcataattc tcttactgtc atgccatccg    8100
taagatgctt ttctgtgact ggtgagtact caaccaagtc attctgagaa tagtgtatgc    8160
ggcgaccgag ttgctcttgc ccggcgtcaa cacgggataa taccgcgcca catagcagaa    8220
ctttaaaagt gctcatcatt ggaaaacgtt cttcggggcg aaaactctca aggatcttac    8280
cgctgttgag atccagttcg atgtaaccca ctcgtgcacc caactgatct tcagcatctt    8340
ttactttcac cagcgtttct gggtgagcaa aaacaggaag gcaaaatgcc gcaaaaaagg    8400
gaataagggc gacacggaaa tgttgaatac tcatactctt cctttttcaa tattattgaa    8460
gcatttatca gggttattgt ctcatgagcg gatacatatt tgaatgtatt tagaaaaata    8520
aacaaatagg ggttccgcgc acatttcccc gaaaagtgcc acctgacgtc taagaaacca    8580
ttattatcat gacattaacc tataaaaata ggcgtatcac gaggccctt cgtcttcaag    8640 aatt                                                                8644

<210> SEQ ID NO 4
<211> LENGTH: 91
<212> TYPE: DNA
<213> ORGANISM: Artificial sequence
<220> FEATURE:
<223> OTHER INFORMATION: Primer p920mrgaF2

<400> SEQUENCE: 4
ctgaggccaa ttaggccaag tttattcttg acattaggga acatgcatga tataataggt    60
aaagtaaaca gatcacaagg aggacgttat c                                   91

<210> SEQ ID NO 5
<211> LENGTH: 34
<212> TYPE: DNA
<213> ORGANISM: Artificial sequence
<220> FEATURE:
<223> OTHER INFORMATION: Primer MBmrgaR2

<400> SEQUENCE: 5
```

```
tgaaggatcc acgcgtccag cagacagaaa gcag                                    34

<210> SEQ ID NO 6
<211> LENGTH: 49
<212> TYPE: DNA
<213> ORGANISM: Artificial sequence
<220> FEATURE:
<223> OTHER INFORMATION: Promoter P920

<400> SEQUENCE: 6
aagtttattc ttgacattag ggaacatgca tgatataata ggtaaagta                   49

<210> SEQ ID NO 7
<211> LENGTH: 642
<212> TYPE: DNA
<213> ORGANISM: Artificial sequence
<220> FEATURE:
<223> OTHER INFORMATION: PCR product of promoter 920 and mrgA

<400> SEQUENCE: 7
ctgaggcctt aagggccaag tttattcttg acattaggga acatgcatga tataataggt       60
aaagtaaaca gatcacaagg aggacgttat cttatgaaaa ctgaaaacgc aaaaacaaat      120
caaacattag ttgagaattc actgaacaca caattatcaa actggtttct tttatactct      180
aagctccacc gtttccattg gtatgtgaaa gggcctcatt tctttacatt gcacgagaaa      240
tttgaagaac tttatgacca tgcggctgaa acagtggata ccatcgctga gcgcctgctg      300
gcgattggcg gacagcctgt tgccacagtg aagaataca ctgagcatgc atctatcaca       360
gacggcggaa acgaaacatc agcatcagaa atggtacaag cattggtaaa cgactacaaa      420
caaatcagca gcgaatctaa attcgtgatc ggcctggctg aagaaaatca agacaatgcg      480
acagcggact tgtttgtcgg attaattgaa gaagttgaaa acaagtgtg gatgctttcc       540 tcttatttag gtaacaaaa aagctgaacc ttaatcgggt tcagcttttt gttttttctt        600
agcttgaact gctttctgtc tgcttgacgc gtggatcctt ca                         642

<210> SEQ ID NO 8
<211> LENGTH: 91
<212> TYPE: DNA
<213> ORGANISM: Artificial sequence
<220> FEATURE:
<223> OTHER INFORMATION: Primer p740mrgaF2

<400> SEQUENCE: 8
ctgaggccaa ttaggcccgg aagtttgttg acacagctcc aggatacaaa tataatgggt       60
cgactaaaca gatcacaagg aggacgttat c                                      91

<210> SEQ ID NO 9
<211> LENGTH: 49
<212> TYPE: DNA
<213> ORGANISM: Artificial sequence
<220> FEATURE:
<223> OTHER INFORMATION: Promoter P740

<400> SEQUENCE: 9
cggaagtttg ttgacacagc tccaggatac aaatataatg ggtcgagta                  49

<210> SEQ ID NO 10
<211> LENGTH: 642
<212> TYPE: DNA
<213> ORGANISM: Artificial sequence
<220> FEATURE:
<223> OTHER INFORMATION: PCR product of promoter 740 and mrgA
```

<400> SEQUENCE: 10

```
ctgaggcctt aagggcccgg aagtttgttg acacagctcc aggatacaaa tataatgggt      60
cgagtaaaca gatcacaagg aggacgttat cttatgaaaa ctgaaaacgc aaaaacaaat     120
caaacattag ttgagaattc actgaacaca caattatcaa actggtttct tttatactct     180
aagctccacc gtttccattg gtatgtgaaa gggcctcatt tctttacatt gcacgagaaa     240
tttgaagaac tttatgacca tgcggctgaa acagtggata ccatcgctga gcgcctgctg     300
gcgattggcg gacagcctgt tgccacagtg aaagaataca ctgagcatgc atctatcaca     360
gacggcggaa acgaaacatc agcatcagaa atggtacaag cattggtaaa cgactacaaa     420
caaatcagca gcgaatctaa attcgtgatc ggcctggctg aagaaatca agacaatgcg      480
acagcggact tgtttgtcgg attaattgaa gaagttgaaa acaagtgtg gatgctttcc       540
tcttatttag ggtaacaaaa aagctgaacc ttaatcgggt tcagcttttt gttttttctt     600
agcttgaact gctttctgtc tgcttgacgc gtggatcctt ca                        642
```

<210> SEQ ID NO 11
<211> LENGTH: 91
<212> TYPE: DNA
<213> ORGANISM: Artificial sequence
<220> FEATURE:
<223> OTHER INFORMATION: Primer p726mrgaF2

<400> SEQUENCE: 11

```
ctgaggccaa ttaggccgag gtgagatttg acactagtag gctacgggac tataatgcgg      60
gaagtaaaca gatcacaagg aggacgttat c                                    91
```

<210> SEQ ID NO 12
<211> LENGTH: 49
<212> TYPE: DNA
<213> ORGANISM: Artificial sequence
<220> FEATURE:
<223> OTHER INFORMATION: Promoter P726

<400> SEQUENCE: 12

```
gaggtgagat ttgacactag taggctacgg gactataatg cgggaagta                 49
```

<210> SEQ ID NO 13
<211> LENGTH: 642
<212> TYPE: DNA
<213> ORGANISM: Artificial sequence
<220> FEATURE:
<223> OTHER INFORMATION: PCR product of promoter P726 and mrgA

<400> SEQUENCE: 13

```
ctgaggcctt aagggccgag gtgagatttg acactagtag gctacgggac tataatgcgg      60
gaagtaaaca gatcacaagg aggacgttat cttatgaaaa ctgaaaacgc aaaaacaaat     120
caaacattag ttgagaattc actgaacaca caattatcaa actggtttct tttatactct     180
aagctccacc gtttccattg gtatgtgaaa gggcctcatt tctttacatt gcacgagaaa     240
tttgaagaac tttatgacca tgcggctgaa acagtggata ccatcgctga gcgcctgctg     300
gcgattggcg gacagcctgt tgccacagtg aaagaataca ctgagcatgc atctatcaca     360
gacggcggaa acgaaacatc agcatcagaa atggtacaag cattggtaaa cgactacaaa     420
caaatcagca gcgaatctaa attcgtgatc ggcctggctg aagaaatca agacaatgcg      480
acagcggact tgtttgtcgg attaattgaa gaagttgaaa acaagtgtg gatgctttcc       540
tcttatttag ggtaacaaaa aagctgaacc ttaatcgggt tcagcttttt gttttttctt     600
```

```
agcttgaact gctttctgtc tgcttgacgc gtggatcctt ca                        642
```

```
<210> SEQ ID NO 14
<211> LENGTH: 88
<212> TYPE: DNA
<213> ORGANISM: Artificial sequence
<220> FEATURE:
<223> OTHER INFORMATION: Primer AN162

<400> SEQUENCE: 14
agactgtccg cggtgtaaaa aataggaata aaggggggtt gacattattt tactgatatg     60
tataatataa tttgtataag aaaatgag                                        88
```

```
<210> SEQ ID NO 15
<211> LENGTH: 32
<212> TYPE: DNA
<213> ORGANISM: Artificial sequence
<220> FEATURE:
<223> OTHER INFORMATION: Primer AN163c

<400> SEQUENCE: 15
gcatacacgc gttgtcacac ctgatgccga cc                                   32
```

```
<210> SEQ ID NO 16
<211> LENGTH: 8152
<212> TYPE: DNA
<213> ORGANISM: Artificial sequence
<220> FEATURE:
<223> OTHER INFORMATION: Plasmid pAN213ban

<400> SEQUENCE: 16
ccgcggtgta aaaataggga ataaaggggg gttgacatta ttttactgat atgtataata     60
taatttgtat aagaaaatga gagggagagg aaacatgatt caaaaacgaa agcggacagt    120
ttcgttcaga cttgtgctta tgtgcacgct gttatttgtc agtttgccga ttacaaaaac    180
atcagccgta aatggcacgc tgatgcagta ttttgaatgg tatacgccga acgacggcca    240
gcattggaaa cgattgcaga atgatgcgga acatttatcg gatatcggaa tcactgccgt    300
ctggattcct cccgcataca aaggattgag ccaatccgat aacggatacg gaccttatga    360
tttgtatgat ttaggagaat tccagcaaaa agggacggtc agaacgaaat acggcacaaa    420
atcagagctt caagatgcga tcggctcact gcattccgg aacgtccaag tatacggaga     480
tgtggttttg aatcataagg ctggtgctga tgcaacagaa gatgtaactg ccgtcgaagt    540
caatccggcc aatagaaatc aggaaacttc ggaggaatat caaatcaaag cgtggacgga    600
ttttcgtttt ccgggccgtg aaacacgta cagtgatttt aaatggcatt ggtatcattt     660
cgacggagcg gactgggatg aatcccggaa gatcagccgc atctttaagt ttcgtgggga    720
aggaaaagcg tgggattggg aagtatcaag tgaaaacggc aactatgact atttaatgta    780
tgctgatgtt gactacgacc accctgatgt cgtggcagag acaaaaaaat ggggtatctg    840
gtatgcgaat gaactgtcat tagacggctt ccgtattgat gccgccaaac atattaaatt    900
ttcatttctg cgtgattggg ttcaggcggt cagacaggcg acgggaaaag aaatgtttac    960
ggttgcggag tattggcaga taatgccgg gaaactcgaa aactacttga ataaaacaag    1020
ctttaatcaa tccgtgtttg atgttccgct tcatttcaat ttacaggcgg cttcctcaca   1080
aggaggcgga tatgatatga ggcgtttgct ggacggtacc gttgtgtcca ggcatccgga   1140
aaaggcggtt acatttgttg aaaatcatga cacacagccg ggacagtcat ggaatcgac    1200 agtccaaact tggtttaaac cgcttgcata cgccttttat ttgacaagag aatccggtta   1260
```

```
tcctcaggtg ttctatgggg atatgtacgg gacaaaaggg acatcgccaa aggaaattcc    1320
ctcactgaaa gataatatag agccgatttt aaaagcgcgt aaggagtacg catacgggcc    1380
ccagcacgat tatattgacc acccggatgt gatcggatgg acgagggaag gtgacagctc    1440
cgccgccaaa tcaggtttgg ccgctttaat cacggacgga cccggcggat caaagcggat    1500
gtatgccggc ctgaaaaatg ccggcgagac atggtatgac ataacgggca accgttcaga    1560
tactgtaaaa atcggatctg acggctgggg agagtttcat gtaaacgatg gtccgtctc    1620 catttatgtt cagaaataag gtaataaaaa aacacctcca agctgagtgc gggtatcagc    1680
ttggaggtgc gtttatttt tcagccgtat gacaaggtcg catcaggtg tgacaacgcg    1740 tgatccagac cagttccctg agcttccgtc agtcggatcc cattgcggaa aatagtcata    1800
ggcatcctgg aattcaatgt tgcgaataat gacgttatca ctcttgattt ggaagtttcc    1860
tcccacgact ttagcgttag tccctgaacc gacgatcgtc gtgtttgcag ggatatccac    1920
catgacccgt gctttttggt ttttctgaga gcgtgctctc gcttcttctt gtgttcccga    1980
cggctctttt ttgccccatg tgctaggatc ataggctttc aaatatttgt ccaaatcata    2040
ctccggatct ttatagtcat ttaggccaag cggcttcaga ttgtcatcca cgttcatgtc    2100
aatcgttccc ttgatataaa tgattttgg cgttgtgttc gtttccttcc ctaatgccga    2160
gacaagctgg tttctgttgc tgacggtata cacatttgag gaggatgctt ttgatccgcc    2220
tgtcgtgccg gtcgagtacg cgccccagcc atcattggat cccaacgtct ggtggcctaa    2280
atcagctgcg ttcgcgccag ctggagtcaa tcctaaaaac aaagccgtag ctaacatcaa    2340
aagggcctcg tgatacgcct atttttatag gttaatgtca tgataataat ggtttcttag    2400
acgtcaggtg gcacttttcg gggaaatgtg cgcggaaccc ctatttgttt attttctaa    2460 atacattcaa atatgtatcc gctcatgaga caataaccct gataaatgct tcaataatat    2520
tgaaaaagga gagtatgag tattcaacat tccgtgtcg cccttattcc cttttttgcg    2580 gcatttgcc ttcctgtttt tgctcaccca gaaacgctgg tgaaagtaaa agatgctgaa    2640
gatcagttgg gtgcacgagt gggttacatc gaactggatc tcaacagcgg taagatcctt    2700
gagagttttc gccccgaaga acgttttcca atgatgagca cttttaaagt tctgctatgt    2760
ggcgcggtat tatcccgtgt tgacgccggg caagagcaac tcggtcgccg catacactat    2820
tctcagaatg acttggttga gtactcacca gtcacagaaa agcatcttac ggatggcatg    2880
acagtaagag aattatgcag tgctgccata accatgagtg ataacactgc ggccaactta    2940
cttctgacaa cgatcggagg accgaaggag ctaaccgctt ttttgcacaa catgggggat    3000
catgtaactc gccttgatcg ttgggaaccg gagctgaatg aagccatacc aaacgacgag    3060
cgtgacacca cgatgcctgc agcaatggca acaacgttgc gcaaactatt aactggcgaa    3120
ctacttactc tagcttcccg gcaacaatta atagactgga tggaggcgga taaagttgca    3180
ggaccacttc tgcgctcggc ccttccggct ggctggttta ttgctgataa atctggagcc    3240
ggtgagcgtg gtctcgcgg tatcattgca gcactggggc cagatggtaa gccctcccgt    3300
atcgtagtta tctacacgac ggggagtcag gcaactatgg atgaacgaaa tagacagatc    3360
gctgagatag gtgcctcact gattaagcat tggtaactgt cagaccaagt ttactcatat    3420
atactttaga ttgatttaaa acttcatttt taatttaaaa ggatctaggt gaagatcctt    3480
tttgataatc tcatgaccaa aatcccttaa cgtgagtttt cgttccactg agcgtcagac    3540
cccgtagaaa agatcaaagg atcttcttga gatcctttt ttctgcgcgt aatctgctgc    3600
ttgcaaacaa aaaaaccacc gctaccagcg gtggtttgtt tgccggatca agagctacca    3660
```

```
actctttttc cgaaggtaac tggcttcagc agagcgcaga taccaaatac tgtccttcta   3720
gtgtagccgt agttaggcca ccacttcaag aactctgtag caccgcctac atacctcgct   3780
ctgctaatcc tgttaccagt ggctgctgcc agtggcgata agtcgtgtct taccgggttg   3840
gactcaagac gatagttacc ggataaggcg cagcggtcgg gctgaacggg gggttcgtgc   3900
acacagccca gcttggagcg aacgacctac accgaactga gatacctaca gcgtgagcta   3960
tgagaaagcg ccacgcttcc cgaagggaga aggcggaca ggtatccggt aagcggcagg   4020
gtcggaacag gagagcgcac gagggagctt ccagggggaa acgcctggta tctttatagt   4080
cctgtcgggt ttcgccacct ctgacttgag cgtcgatttt tgtgatgctc gtcaggggg   4140 cggagcctat ggaaaaacgc cagcaacgcg gcccgacctc gagctggata cttcccgtcc   4200
gccaggggga catgccggcg atgctgaagg tcgcgcgcat tcccgatgaa gaggccggtt   4260
accgcctgtt tgaggatata gtaatctttc taaatagctt tggattggag gagtatgggg   4320
agatcaggga atgagtttat aaaataaaaa agcacctga aaggtgtct ttttttgatg   4380 gttttgaact tgttctttct tatcttgata catatagaaa taacgtcatt tttattttag   4440
ttgctgaaag gtgcgttgaa gtgttggtat gtatgtgttt taaagtattg aaaacccta   4500 aaattggttg cacagaaaaa ccccatctgt taaagttata agtgactaaa caataacta   4560 aatagatggg ggtttctttt aatattatgt gtcctaatag tagcatttat tcagatgaaa   4620
aatcaagggt tttagtggac aagacaaaaa gtggaaaagt gagaccatga tgcttaggaa   4680
gacgagttat taatagctga ataagaacgg tgctctccaa atattcttat ttagaaaagc   4740
aaatctaaaa ttatctgaaa agggaatgag aatagtgaat ggaccaataa taatgactag   4800
agaagaaaga atgaagattg ttcatgaaat taaggaacga atattggata aatatgggga   4860
tgatgttaag gctattggtg tttatggctc tcttggtcgt cagactgatg ggccctattc   4920
ggatattgag atgatgtgtg tcatgtcaac agaggaagca gagttcagcc atgaatggac   4980
aaccggtgag tggaaggtgg aagtgaattt tgatagcgaa gagattctac tagattatgc   5040
atctcaggtg gaatcagatt ggccgcttac acatggtcaa tttttctcta ttttgccgat   5100
ttatgattca ggtggatact tagagaaagt gtatcaaact gctaaatcgg tagaagccca   5160
aacgttccac gatgcgattt gtgcccttat cgtagaagag ctgtttgaat atgcaggcaa   5220
atggcgtaat attcgtgtgc aaggaccgac aacatttcta ccatccttga ctgtacaggt   5280
agcaatggca ggtgccatgt tgattggtct gcatcatcgc atctgttata cgacgagcgc   5340
ttcggtctta actgaagcag ttaagcaatc agatcttcct tcaggttatg accatctgtg   5400
ccagttcgta atgtctggtc aacttttccga ctctgagaaa cttctggaat cgctagagaa   5460
tttctggaat gggattcagg agtggacaga acgacacgga tatatagtgg atgtgtcaaa   5520
acgcatacca ttttgaacga tgacctctaa taattgttaa tcatgttggt tacgtattta   5580
ttaacttctc ctagtattag taattatcag cggccccact aatactaagt tcagctaata   5640
aaaaaatttg ctaaagaact ccagctggat ttcactgatg agaatatcgt cggagataaa   5700
tataataatt ccacggacta tagactatac tagtatactc cgtctactgt acgatacact   5760
tccgctcagg tccttgtcct ttaacgagga ttgttaccga ctaagaaaat gccgtcaaat   5820
ccgctcgcca tgacttcacg tcgacccgca ccgcttgat ttataacatt tgatttcaca   5880
ttagcagaag catcaatcga tccatgcaga gacggcgtcc agccgacaga agagctcagc   5940
ccgtttgcag ccgatgcgtt gatctgtgtg ccgttcagca acgtgccgga gtcatataaa   6000
gccgttcccc cgctgaatac gctgatcgtt ttagcagctg acagtcccgg tacgtcaatg   6060
```

```
acattgtttt gggcatagat tttagatgac tttccgattc cccatgcata gctaaaagga    6120
taacttgaag agcttgtgct tccttcataa tagttgttgt atacgtgcac ttgcccgaag    6180
cggactctcg gcgcgcgctg gacaatattt ttatagcggt tatgatgcag cgtaattttt    6240
aatttgccgt catcggaggt tttgctgtca cttgatccga aaatggagct tttatcatga    6300
tcgtgataat agttgtagga catcgtgata tagttagcac cgttggaagc atccgtttgg    6360
ccgtcatggt gctgatattt tcttccataa tatttcggtg atgtgctgtc cggacgcgaa    6420
ccgtgtcggc gatataggcg ccagcaaccg cacctgtggc gccggtgatg ccggccacga    6480
tgcgtccggc gtagaggatc tggagctgta atataaaaac cttcttcaac taacggggca    6540
ggttagtgac attagaaaac cgactgtaaa agtacagtc ggcattatct catattataa    6600
aagccagtca ttaggcctat ctgacaattc ctgaatagag ttcataaaca atcctgcatg    6660
ataaccatca caaacagaat gatgtacctg taaagatagc ggtaaatata ttgaattacc    6720
tttattaatg aattttcctg ctgtaataat gggtagaagg taattactat tattattgat    6780
atttaagtta aacccagtaa atgaagtcca tggttatgtc tttgtatccc gtttgtatta    6840
cttgatcctt taactctggc aaccctcaaa attgaatgag acatgctaca cctccggata    6900
ataaatatat ataaacgtat atagatttca taaagtctaa cacactagac ttatttactt    6960
cgtaattaag tcgttaaacc gtgtgctcta cgaccaaaac tataaaacct ttaagaactt    7020
tcttttttta caagaaaaaa gaaattagat aaatctctca tatctttat tcaataatcg    7080 catccgattg cagtataaat ttaacgatca ctcatcatgt tcatatttat cagagctcgt    7140
gctataatta tactaatttt ataaggagga aaaaatatgg gcattttag tattttgta    7200 atcagcacag ttcattatca accaaacaaa aaataagtgg ttataatgaa tcgttaataa    7260
gcaaaattca tataaccaaa ttaaagaggg ttataatgaa cgagaaaaat ataaaacaca    7320
gtcaaaactt tattacttca aaacataata tagataaaat aatgacaaat ataagattaa    7380
atgaacatga taatatcttt gaaatcggct caggaaaagg ccattttacc cttgaattag    7440
taaagaggtg taatttcgta actgccattg aaatagacca taaattatgc aaaactacag    7500
aaaataaact tgttgatcac gataatttcc aagttttaaa caaggatata ttgcagttta    7560
aatttcctaa aaaccaatcc tataaaatat atggtaatat accttataac ataagtacgg    7620
atataatacg caaaattgtt tttgatagta tagctaatga gatttattta atcgtggaat    7680
acgggtttgc taaaagatta ttaaatacaa aacgctcatt ggcattactt ttaatggcag    7740
aagttgatat ttctatatta agtatggttc caagagaata ttttcatcct aaacctaaag    7800
tgaatagctc acttatcaga ttaagtgaaa aaaaatcaag aatatcacac aaagataaac    7860
aaaagtataa ttatttcgtt atgaaatggg ttaacaaaga atacaagaaa atatttacaa    7920
aaaatcaatt taacaattcc ttaaaacatg caggaattga cgatttaaac aatattagct    7980
ttgaacaatt cttatctctt ttcaatagct ataaattatt taataagtaa gttaagggat    8040
gcataaactg catcccttaa cttgtttttc gtgtgcctat ttttgtgaa tcgacctgca    8100 ggcatgcaag ctttttcaat tcatccgtca cagtctcagg atgattgatc ac            8152
```